United States Patent
Ridde

(10) Patent No.: US 9,370,374 B1
(45) Date of Patent: Jun. 21, 2016

(54) SURGICAL ACETABULAR GRATER ADAPTER AND ASSOCIATED METHOD

(71) Applicant: Michael Paul Ridde, Hurricane, WV (US)

(72) Inventor: Michael Paul Ridde, Hurricane, WV (US)

(*) Notice: Subject to any disclaimer, the term of this patent is extended or adjusted under 35 U.S.C. 154(b) by 0 days.

(21) Appl. No.: 14/527,896

(22) Filed: Oct. 30, 2014

Related U.S. Application Data

(60) Provisional application No. 61/901,780, filed on Nov. 8, 2013.

(51) Int. Cl.
*A61B 17/16* (2006.01)
(52) U.S. Cl.
CPC .................. *A61B 17/1666* (2013.01)
(58) Field of Classification Search
CPC ............................ A61B 17/16; A61B 17/164
USPC .......................................... 606/79–85, 86 R
See application file for complete search history.

(56) References Cited

U.S. PATENT DOCUMENTS

| 2007/0191854 A1* | 8/2007 | Grim ................. | A61B 17/1666 606/80 |
| 2008/0195101 A1* | 8/2008 | Lechot .............. | A61B 17/1617 606/79 |

* cited by examiner

*Primary Examiner* — Christopher Beccia

(57) ABSTRACT

An adapter and associated method is provided. One of the many embodiments of the present application is comprised of a one-piece adapter attachable along the backside of the shell component of an acetabular reaming tool, and having a geometric configuration approximating an annular collar. The adapter has a smooth peripheral surface including an area of greater circumference converging to an area of lesser circumference. When the adapter attaches to an acetabular grater shell component, the area of greater outer circumference is proximal to, and traverses the theoretical equator of, the shell component, and the area of lesser outer circumference is distal to the shell component and is the leading end of the adapter when the reaming tool is extracted from the surgical site. The contours and smooth surface of the adapter facilitate fast, safe, unimpeded extraction.

26 Claims, 8 Drawing Sheets

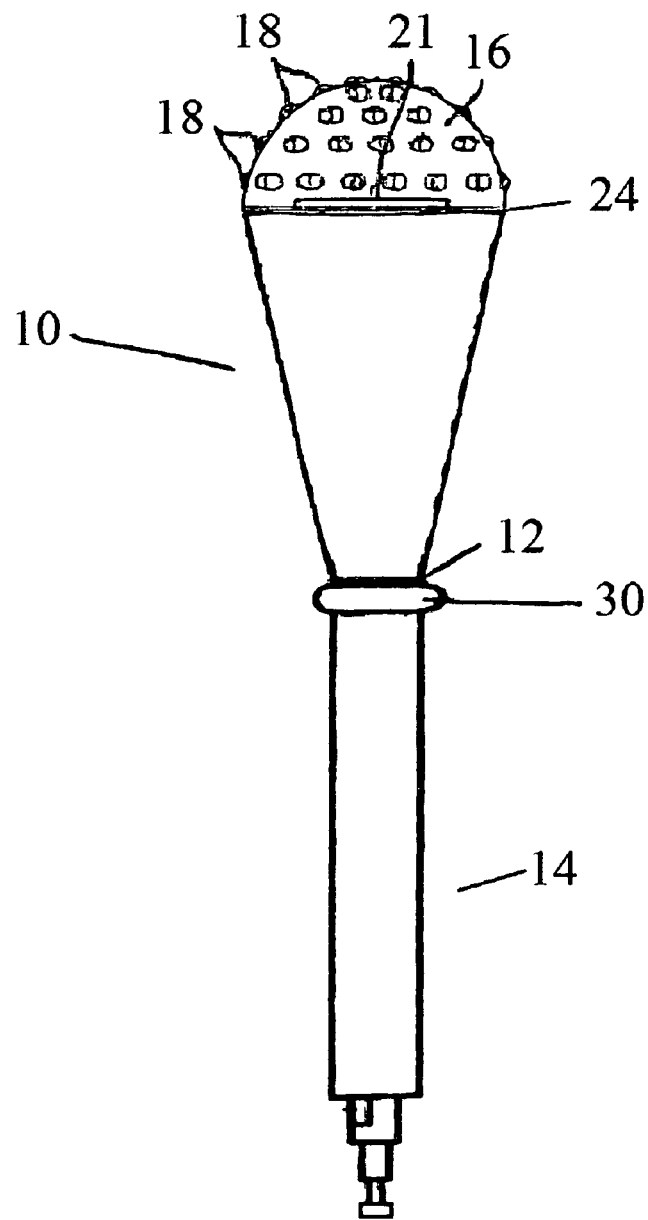
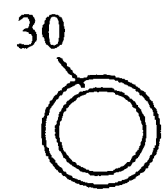
FIG. 8b
FIG. 8a

SURGICAL ACETABULAR GRATER ADAPTER AND ASSOCIATED METHOD

CROSS REFERENCE TO RELATED APPLICATIONS

This application claims priority and benefit to U.S. provisional patent application Ser. No. 61/901,780, filed Nov. 8, 2013, entitled "Surgical Reamer Adapter and Associated Method."

BACKGROUND OF THE INVENTION (a) Technical Field of the Invention

The present application generally pertains to a method and device used to mitigate against soft tissue injury during joint replacement surgery. More specifically, the present application relates to a method and device for moderating injury and tissue damage that occurs when extracting a reaming tool during joint replacement surgery.

It is fundamental that, when tissue damage is minimized during the surgery process, the patient's ability to quickly regain normal levels of physical function and avoid post-operation pain and protracted rehabilitation is enhanced.

Surgically-implanted prosthetic joints are commonly used to replace an arthritic and diseased or damaged joint within the human body. For ball and socket joints, such as hip or shoulder joints, the desired result is to have an artificial ball arising from one bone, set against or secured to and articulating within an implanted artificial socket in a manner that approximates a healthy natural joint. The features and function of artificial ball and socket joints are known to those of ordinary skill in the art, and thus need not be described in detail herein.

The surgical process for implanting artificial hip joints includes the use of a tool commonly known as an acetabular grater. The acetabulum is the person's natural hip socket. The acetabular grater is used for reaming the inner surface of this acetabular socket to create a surface within the socket that is suitable for accommodating the installation of a generally concave, artificial acetabular cup and liner. A typical acetabular grater is comprised of a modular metal shell component, having a convex, substantially hemispherical geometrical configuration. A shell component, which is the acetabular grater, typically is mounted to a long metal shaft commonly known as a reamer handle, which connects along the central part of the cavity located on the backside of acetabular grater. The reamer handle forms an axis of rotation for the acetabular grater. A source of rotary power in the form of a surgical drill is connected to the reamer handle and turns the rotating portion of the reamer handle along with the acetabular grater, thus allowing the surgeon to transmit torque to achieve the cutting and grating of bone and cartilage within the joint socket.

Cutting is achieved via a plurality of sharp, raised edges located along the convex surface of the acetabular grater. Cut fragments of bone and cartilage enter, and are collected in, the body of the acetabular grater through an opening located along each of the plurality of sharp raised edges. Each shell component grater has a designated diameter. Based upon the size of the patient's natural joint socket, reaming begins with the use of an acetabular grater that is smaller than the natural joint socket, and then progresses incrementally in size until all the joint cartilage or other soft tissue or bony debris is removed, and the acetabulum is reamed to the desired size and condition. As each shell of the grater fills with bone and cartilage fragments during the reaming process, they are extracted from the joint, then the grater is changed to a larger size, and reaming resumes. The features and functions of an acetabular reaming system and all its components are known to those of ordinary skill in the art, and thus need not be described in further detail herein.

There is limited space to accommodate and accept the insertion of an acetabular grater into the surgical incision site opening during the reaming process due to soft tissues, contractures, and bone overlying and or enveloping the acetabulum. This is especially the case during total hip replacement surgeries and particularly those that are performed through an anterior surgical approach, which is typically a smaller more state of the art minimally invasive incision and technique. This makes advancing the acetabular grater into the acetabulum somewhat challenging at times. Even more challenging is extraction of this acetabular grater following its use. It is during each of these commonly difficult extractions that the backside of the prior art acetabular grater system, due to its flat shape and steep edged corners, lodges or snags and hangs up on the enveloping soft tissues and bone. This causes a significant increase in force, manipulation, and time that is needed to extract the grater, thus simultaneously causing significantly more soft tissue and vascular damage. Specifically, this relative difficulty of extraction starts a negative domino effect by increasing the time for completion of surgery, thereby increasing the time the patient is under anesthesia, which then increases unnecessary risks to the patient including but not limited to increasing the risk for unintended soft tissue and vascular damage. This also increases the physical force needed to extract the acetabular grater which then causes further damages to tissues. By default this difficult extraction then fatigues and frustrates the surgeon, and causes other related problems, not to mention that this also is increasing the financial cost to the patient and the facility all the while.

(b) Description of the Relevant Art

A considerable number of patents relate generally only to surgical acetabular reamers. Many of these inventions address the access to the acetabulum, the precision of the reaming, the removal of bone, and the connection apparatus of the reamer device. Some of these inventions attempt to decrease soft tissue damage.

In U.S. Pat. No. 8,784,422 B2, by Lechot, Desarzens, and White discloses an acetabular reamer tool for cutting a hemispherical cavity in bone. Due to the modified shape of the cutting surfaces, this device sets forth to allow for cutting of the bone more precisely. They further state that it allows the tool to be more linearly advanced without having to "rock" the tool by changing the orientation of the cutting approach in order to achieve the full cut. This is all accomplished while simultaneously employing the linear cut to be guided by accurate visual confirmation by the user.

In U.S. Pat. No. 8,235,996 B2, by Parker also discloses an acetabular reamer tool for cutting a hemispherical cavity in bone. This patent sets forth a modified shape of the reamer (grater) shell that allows it to be more low profile and only partially hemispherical. In essence, instead of the traditional prior art reamers that are fully hemispherical on their leading end that is introduced into the acetabulum (but still flat on their backside), this device is more ovular. It still follows a circumferential rotation cutting a perfectly hemispherical cavity in the bone as its prior art counterparts (because of its two remaining hemispherical ends), but its sides have been taken away and replaced by a planar or concave shape making it more ovular in overall shape. This lower profile design purports to decrease soft tissue damage upon inserting the reaming tool into the surgical site, and during reaming, and upon extraction, but due to its ovular shape it does "wobble" a little upon its axis during rotation.

U.S. Pat. No. 7,621,915 B2, by Frederick, Miller, and Walter is very similar to the Parker invention in many respects. Although they too attempt to set forth a low profile acetabular reamer that is primarily ovular in shape having the sides removed and replaced with a planar surface, it differs in its positioning of the teeth or cutting edges. Even further, in one embodiment it has a traditionally hemispherical reamer with respect to its leading edge during insertion (like the traditional prior arts), but it has removed the teeth or cutting edges completely on opposing sides so that the opposing sides of the hemisphere are smooth. The backside of the reamer shells (that connects to the reamer handle) of all the embodiments of this invention including that of the aforementioned Parker's, remain flat shaped.

U.S. Pat. No. 7,559,928 B2, by Johnson, Engh, and Travanty is an apparatus and method directed to accomplish accurate bone preparation through a limited surgical exposure for hip replacement surgeries. This is not simply a reamer but is rather a collective system comprised of multiple parts including its own reamer handle to accomplish the desired goal. Its primary delineating feature that contrasts the other prior art is that it positions the reamer shell sideways on its reamer handle. Instead of a reamer shell that is connected in a linear configuration with the reamer handle with direct axial rotation parallel to and in line with the linear reamer handle (as a traditional drill and drill bit), it positions the reamer shell and its axis of rotation perpendicular to the side of the linear shaft of the reamer handle. In doing this the reamer shell is introduced into the surgical site with its side being the leading edge. This essentially works, at least during introduction and extraction of the reamer, as do the low profile reamers of the two previously mentioned patents by introducing and extracting a tool with less surface area by the leading edge.

U.S. Pat. No. 7,220,264 B1, by Hershberger sets forth a reamer for reaming of an acetabulum during a minimally invasive procedure. This reamer, like all those of the traditional prior art reamers generally includes a reaming or scraping portion, which are aligned substantially along a single meridian of a hemisphere, and stabilizing portions to assist in ensuring a selected reaming orientation. However, they further disclose at least two separately opposing and sharp hook shaped protective "wings." The wing structures are part of the actual shape and design of this reamer for the purpose in theory to attempt to assist in removing the reamer to decrease soft tissue damage during reaming. In some embodiments however, the backside of the reamer itself is a continuous tapered rim. Additionally they disclose large open areas in the cutting portion of the reamer shell that, similar in purpose to Lechot, Desarzens, and White, is directed at being guided by more accurate visual conformation to achieve more precise reaming depth into the acetabular socket.

U.S. Pat. No. 5,462,548 A, by Pappas, and Buechel discloses an acetabular reamer with a more efficient locking mechanism. This invention is directed at preventing unintended separation of the reamer head from the reamer shaft when the surgeon is withdrawing the reamer head from the acetabular cavity. They also include a reamer shaft, a mounting cap, a locking spring, and a sleeve in this system. Although the primary intention is the improved locking mechanism, in theory, (although this is not disclosed) this would also decrease soft tissue damage because of not having to use other tools to retract and explore the acetabular cavity to retrieve an unintentionally disengaged reamer head.

Henceforth, as can be clearly seen, the prior art does not provide any device or adequate method that specifically addresses all these issues by having all the benefits with none of the detriments. Therefore, there remains the risk of tissue damage and consequent problems caused by the flat shape and sharp, steep edges of the backside of the primary common use acetabular grater shell components during their extraction from the surgical site. Even the protective "wings" mentioned in one of the aforementioned prior art does not adequately address this issue. In fact due to the deficient continuity and separate hook shape of the wings, they in fact will cause the opposite effect by grabbing soft tissue during rotation and during the ingress and egress of the reamer causing more tissue damage than the normal traditional reamers. Furthermore, even in its alternative embodiments, that invention would be more costly to surgical facilities and orthopedic companies because it requires a total abandonment of all the prior art reamers in current use and a total redesign since this is itself a reamer. Therefore, there remains a great need for a safe, effective, cost efficient and universal adapter that can be applied to any size and style of acetabular graters. The present application addresses all these issues by enabling each insertion and extraction of the acetabular graters to be performed relatively quickly and easily, while avoiding and minimizing damage to soft tissues that have been caused by all the prior art shell components. This present application herein causes a positive domino effect by decreasing the time for completion of surgery, thereby decreasing the time the patient is under anesthesia, which then decreases unnecessary risks to the patient including but not limited to decreasing the risk for unintended soft tissue and vascular damage. This also decreases the physical force needed to extract the acetabular grater which then helps prevent further damage to soft tissues. By default this quicker and easier extraction then does not fatigue or frustrate the surgeon, and helps prevent other related problems. The present application is also inexpensive to mass produce and is cost effective for the patient and the medical facility. Additionally, the preferred embodiment of the present application does not require any modification to the prior art acetabular grater or its components, nor does it change the sterilization process, the surgery technique, or the appearance of the acetabular grater shell component on X-ray fluoro during the reaming procedure.

SUMMARY OF THE INVENTION

The present application provides a unique, safe, economical, and effective way to solve the problems inherent in the insertion and even more so the extraction of an acetabular or glenoid reamer/grater shell component into and from a patient's surgical site throughout the reaming procedure, particularly during but not limited to, an anterior hip or a shoulder replacement surgery. More specifically it does this via a method of adding and utilizing a tapered ring adapter interlockably connected to and removable from the backside of the shell component of a standard acetabular grater, thereby creating a smooth flush tapered and contoured transition from the top of the adapter to the backside of the grater. The method and force of extraction then become less due to a decreased resistance due to the tapered contour and smooth glide of the adapter against the bone and soft tissues during extraction. The adapter also supports the enveloping soft tissues during insertion. Although the contours of a reamer handle and said reamer/graters and their components may vary depending upon manufacturer and model, the adapter of the present application can be customized during production to accommodate such variations. Furthermore, as there are multiple incremental sizes of the current acetabular grater shell components in any particular surgical instrument set, so will there be matching sizes of the adapters for each and every size of the individual graters. Regardless of the manufacturer or model or shape of the reamer/graters, whether they are traditional or minimally invasive, the current application pertaining to its method and device can be universally adapted to fit and attach and then be utilized. It should be noted of the embodiments herein that any combination of materials or locking mechanisms can be used alone or in combination with each other to achieve the desired purpose.

In the preferred embodiment, the adapter generally has a symmetrical body with a smooth outer periphery, with an arcuate (curved) taper, including a bottom end with an area of greater outer circumference gradually converging and tapering to a top end towards the axis of rotation having an area of lesser outer circumference. The inner diameter generally will be at a vertical 90 degree angle with no taper, or may mimic the angle of the outer diameter taper to any degree, or may be the opposite angle respectively top to bottom from the outer diameter or any circumferential combination. When the adapter attaches to an acetabular reamer, the bottom end is proximal to, and in intimate direct or close contact with, the backside of the shell component, so that the area of greater outer circumference is flush with and traverses the theoretical equator of the shell component, and the top end is distal to the backside of the shell component and is at a lesser outer circumference An exemplary embodiment of the tapered adapter of the present application is comprised of durable, lightweight, corrosion-resistant, surgical grade, radiolucent material, such as, but not limited to, celcon, ultem, carbon fiber, composite, polymer, other plastics, or any combinations thereof.

In some embodiments, the adapter may be comprised of a radiopaque corrosion-resistant black oxinium, or any other metal alloy including but not limited to stainless steel, titanium, nickel, aluminum, or any number of combinations of any used surgical metals, precious metals, or semi-metallics.

In some embodiments, the adapter may be comprised of a radiopaque ceramic, or porcelain or other hard material with or without glaze.

In some embodiments, the adapter may be transparent or semitransparent, while other embodiments may be of any tinted or solid color of the spectrum and/or any combination thereof.

In some embodiments, the adapter may not necessarily be a continuous tapered hemispherical ring shape but may be ovular or any other shape that matches the backside shape of any reamer/grater. An example is where some prior art low profile reamers have two hemispherical ends but the sides have been taken away and replaced with a planar or concave shape but this does not limit the scope of options to be compatible with the various shapes and configurations that exist for the backside of reamer/graters.

In some embodiments the adapter may have notches, holes, spaces, grooves or slots on the inner and/or outer portions to allow it to receive a tool that would be used to attach and remove the adapter from the reamer/grater.

In some of the many embodiments, the tapered adapter attaches to the grater shell component by an interlocking mechanism in any material or combination of materials; radiolucent, or radiopaque, and is a modular one or two or more-piece, or non-modular one-piece unibody as part of the adapter itself.

In the preferred embodiment, an interlocking mechanism may include any variation, position, or number of curved locking bars or tabs, with or without de-rotational bumps, that twist on and off by complete clockwise or counterclockwise rotation/s or partial rotation with the hand or a tool and may also secondarily be used as a buttress.

In some embodiments, an interlocking mechanism may include any variation, position, or number of male or female threads, with or without de-rotational bumps, that twist on and off by complete clockwise or counterclockwise rotation/s or partial rotation by the hand or a tool. These particular types of embodiments may or may not include an additional plastic, metal alloy, semi metallic, or other hard material that is radiolucent or radiopaque that comprises a male or female threaded ring added to the reamer prior to attachment of the adapter to allow the reamer to receive these different embodiments of the adapter.

In some embodiments, an interlocking mechanism may include any variation, position, or number of snap clips or hooks or loops or any combination thereof.

In some embodiments, an interlocking mechanism may include any variation, position or number of leaver arms alone or in combination with any variation, position, or number of snap clips or hook loops.

In some embodiments, an interlocking mechanism may include any variation, position, or number of screws, rivets, male studs, or adhesives or any combination thereof.

In some embodiments the adapter may have an interlocking mechanism that allows it to attach by compression press-fit, or cold weld.

In some embodiments, an interlocking mechanism may include a rim lip that traverses the inner circumference of the bottom end and is contoured to firmly interlock with the backside of the shell component as a buttress that may be alone or in any variation, position, or combination of any of the aforementioned interlocking mechanisms.

In some embodiments particularly if the adapter is of any combination of weldable metal alloy it could be attached by permanently welding it to the backside of the reamer with a smooth or grooved transition. In this particular embodiment the bottom inner diameter of the adapter is preferably to be flush to the inner diameter of the backside of the reamer. In a preferred embodiment the bottom outer diameter of the adapter will be preferably flush to the outer diameter of the backside of the reamer.

In some embodiments, a particular kind of interlocking mechanism may be used alone or in combination with one or more other kinds of interlocking mechanisms, with or without de-rotational bumps, and may be permanently attached to the shell component or may removable, may be a snug fit or may toggle or have a space.

In some embodiments the taper may be curved as in the present application, or the taper may be flat, straight, wavy, ribbed, or a combination of any of these at any degree taper. In any case, the bottom outer diameter remains a greater diameter than the top outer diameter that is a lesser diameter, and the bottom outer diameter is preferably to be flush with the outer diameter of the backside of the reamer.

In some embodiments the adapter could be permanent or disposable. In some embodiments of the present application, the reamer shell component and the adapter are manufactured or cast molded as a single one-piece unibody unit.

In the preferred embodiment, the geometric configuration of the adapter of the present application approximates a tapered annular collar or tapered O-ring. In other embodiments the geometric configuration of the adapter approximates a truncated cone.

In some embodiments, the geometric configuration of the adapter approximates an ogive.

In some embodiments, the geometric configuration of the adapter is approximately hemispherical.

In some embodiments, the adapter of the present application has a flat, circular, substantially closed bottom end including a substantially circular first aperture located radially, and having a smooth peripheral surface including a greater outer circumference converging to a top end having a lesser outer circumference and an inner circumference defined by a second aperture.

In some embodiments, the adapter of the present application attaches to the shaft or end of an acetabular reamer handle, so that the shaft traverses through and beyond said first and second apertures being short or elongated, and describes a centrally-located longitudinal axis of rotation within the adapter interior. The circumferences of first aperture and second aperture approximate, or are nominally larger than, the outer circumference of the portion of shaft to which each aperture, respectively, is proximal. The geometry of said first and second apertures thus compliments the dimensions of the shaft to allow free 360° rotation of the adapter around said longitudinal axis.

In some embodiments of the present application, a centrally-located cylindrical passageway traverses the adapter longitudinally and describes an axial through bore within the adapter interior, configured to accommodate the shaft of a reaming tool to allow free 360° rotation of the adapter along an axis.

In some embodiments where the adapter attaches to the shaft of a reaming tool, a flexible, elastomeric band or ring may fit snugly around the outer circumference of the acetabular reamer's shaft and in intimate contact with the top end. The ring has an outer circumference greater that the circumference of the second aperture. When the adapter is properly positioned along the reamer shaft, the ring helps to maintain contact between the backside of the shell component and the bottom end of the adapter while the reaming tool is in use.

In some embodiments, the adapter is comprised of two pieces, which may attach to one another to enclose a section of reamer shaft. When the two pieces attach to one another, two seams extend longitudinally along the body of the adapter, on a plane including the rotational axis, and each seam is approximately 180° apart from the other.

In some embodiments, the adapter of the present application has a substantially solid, non-hollow, interior.

In some embodiments, the adapter has a substantially hollow interior.

In some embodiments, the adapter of the present application comprises a bottom end having an area of greater outer circumference that traverses the theoretical equator of the shell component, and a smooth peripheral surface tapering from the area of greater outer circumference to a top end having an area of lesser outer circumference.

Additional utility and features of the device of the present application will become more fully apparent to those skilled in the art by reference to the following drawings, which illustrate some of the primary features of some of the embodiments.

BRIEF DESCRIPTION OF THE DRAWINGS

FIG. 1a, and FIG. 1b are preferred embodiments of the tapered adapter of the present application.

FIG. 4a, and FIG. 4b are preferred embodiments of the tapered adapter of the present application.

FIG. 8a, and FIG. 8b is an embodiment where the adapter of the present application is taller and more elongated and is attached to a reamer handle instead of an acetabular grater. An additional locking washer is also shown slipped over the reamer handle.

DETAILED DESCRIPTION OF EMBODIMENTS OF THE INVENTION

Figure 1A:
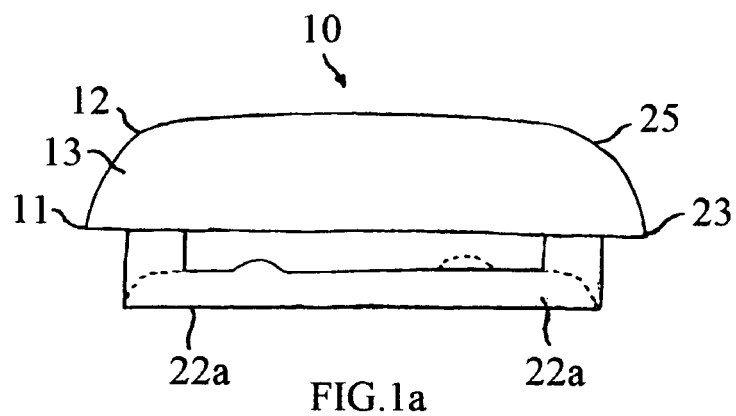
FIG. 1a, FIG. 1b, and FIG. 1c are a side view of three embodiments of the tapered adapter of the present application.
Figure 1B:
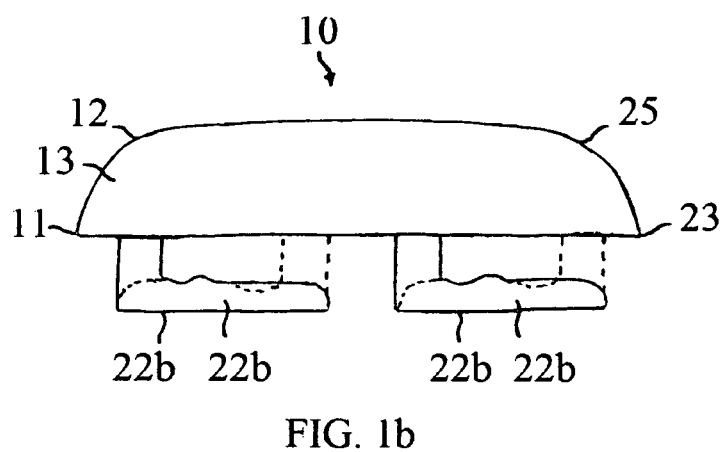
Figure 1C:
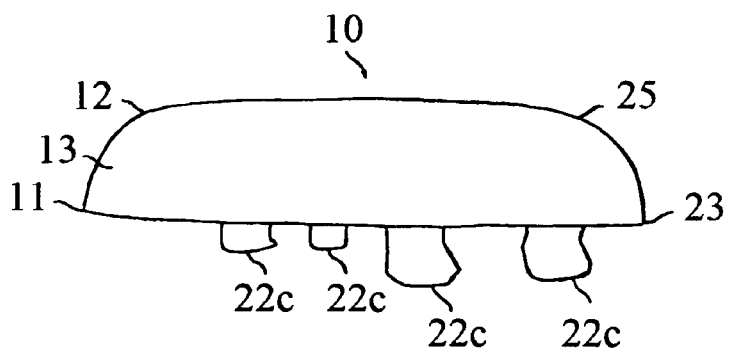

FIG. 1a, FIG. 1b, and FIG. 1c are the side view of three of the embodiments of the tapered adapter 10 including variations of the locking portion 22. The locking portion 22 is further defined as 22a in FIG. 1a, 22b in FIG. 1b, and 22c in FIG. 1c, and 22d shown later in FIG. 7c. FIG. 1a is the preferred embodiment (having a two curved bar reverse twist locking portion 22a) that attaches to the cross bar 19 (and may also act as a buttress against the inner diameter of backside 17) of the exemplary grater shell of FIG. 3a. FIG. 1a is the side view of the embodiment shown in FIG. 4a. FIG. 1b is the preferred embodiment (having a 4 curved bar reverse twist locking portion 22b) that attaches to the cross bars 19 (and may also act as a buttress against the inner diameter of backside 17) of the exemplary grater shell of FIG. 3b. FIG. 1b is the side view of the embodiment shown in FIG. 4b. FIG. 1c is an embodiment (having a 4 clip locking portion 22c) that attaches to the cross bar 19 and the inner rim lip of backside 17 of the exemplary grater shell of FIG. 3a. FIG. 1c is the side view of the embodiment shown in FIG. 4c. Other embodiments utilizing locking portions with clip variations (not shown) can be attached to the exemplary grater shell of FIG. 3b. The embodiments in FIG. 1 shows bottom end a (bottom portion) 11 with an area of greater outer circumference and bottom outer apex 23, tapering to top end (top portion) 12 having an area of lesser outer circumference 25. The embodiments in FIG. 1 has peripheral surface (outer portion) 13 that is generally rounded/tapered. In some embodiments, peripheral surface 13 may be generally flat, straight, wavy, slanted, beveled, or a combination of any of these at any degree taper. In any case, the bottom outer diameter remains a greater diameter than the top outer diameter that is a lesser diameter.

Figure 2:
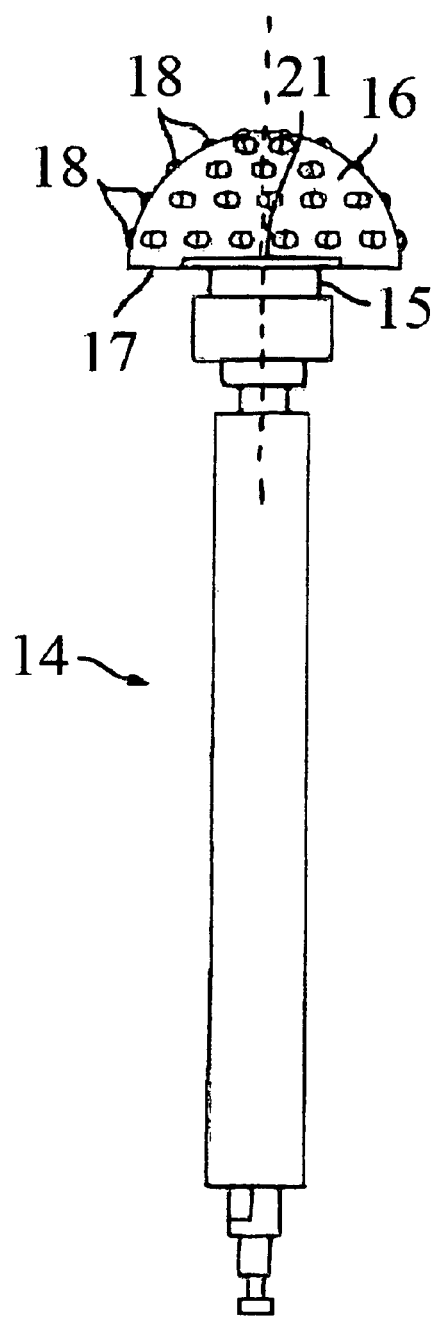
FIG. 2 is a side view of an exemplary acetabular grater shell (reamer) component attached to a straight reamer handle.

FIG. 2 is a side view of exemplary acetabular grater shell component 16. The assembled reamer handle 14 connects to grater shell component 16. The reamer handle 14 connects at its distal most end 15 to a central location along backside 17 of grater shell component 16, and forms rotational axis 21 around which grater shell component 16 rotates when the reamer is in use. Located along the convex surface of grater shell component 16 is a plurality of cutting edges 18 which perform the acetabular reaming function when acetabular reamer is in use. For reaming to be performed, ultimately the entire assembled reamer unit would be connected to a surgical drill at the proximal most end 9 of the reamer handle 14 opposite end from distal most end 15 of reamer handle 14.

When, for example, hip replacement surgery is performed, grater shell component 16 that is attached to acetabular reamer handle 14 is inserted into the patient's body through a small surgical incision overlying the joint undergoing surgery. The convex outer surface of the acetabular grater shell component 16 is introduced to the acetabulum to perform the reaming of the acetabular socket. However, introduction of the acetabular grater shell component 16 into the patient's body is relatively easy, compared to removal of the grater shell component 16 following its use. This is because backside 17 of grater shell component 16 is contoured with a flat shape and steep edged corners, that causes it to lodge or snag and hang up on the enveloping soft tissues and bone when the grater shell component 16 is withdrawn. Thus, the potential for soft tissue damage increases as grater shell component 16 is pulled away from the acetabulum and exiting from the surgical incision through those various layers of enveloping soft tissues.

Figure 3A:
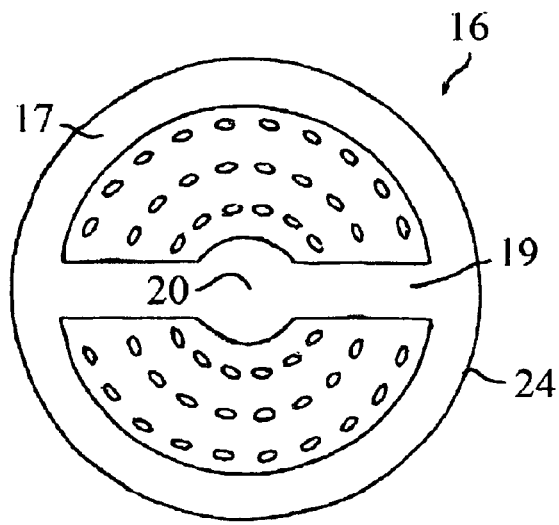
FIG. 3a, and FIG. 3b are a front face on view of the backside of two of the most commonly used exemplary acetabular grater shell components.
Figure 3B:
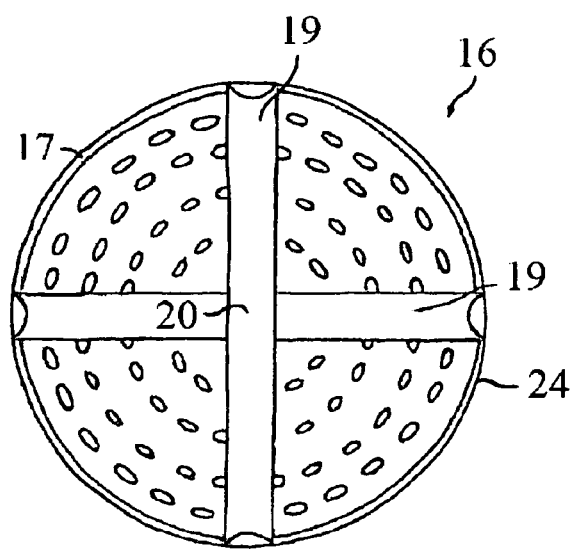

FIG. 3a, and FIG. 3b are a front face on view of backside 17 of two of the most commonly used grater shell components 16. Operably part of, and traversing the diameter of, backside 17 of grater shell component 16 is one or more cross bar/s 19. The backside 17 of grater shell 16 of FIG. 3a has one planar cross bar 19. The backside 17 of grater shell 16 of FIG. 3b has two rounded cross bars 19. Center 20 defines rotational axis 21 of shell component 16. Cross bar/s 19 is/are perpendicular to rotational axis 21. Cross bar/s 19 and center 20 of grater shell component 16 is the part in which the distal most end 15 of the reamer handle 14 connects. The entire surface of the entire circumference of backside 17 of grater shell component 16 is where the bottom end 11 of an embodiment of tapered adapter 10 will be in intimate and direct contact with each other. The theoretical equator 24 is the outermost circumference of backside 17 of grater shell 16. At the general region where cross bar/s 19 meets the inner diameter of backside 17 is where some embodiments of the present application will attach by various interlocking mechanisms 22. In preferred embodiments of the tapered adapter 10 of the present application, the interlocking mechanisms 22 will interlock directly to cross bar/s 19. In some embodiments of the tapered adapter 10 of the present application, the interlocking mechanisms 22 will interlock to backside 17, or with both in various positions, configurations, or combinations. In the preferred embodiments of the tapered adapter 10 of the present application, it will attach to the grater shell 16 while leaving space for the distal end 15 of reamer handle 14 to connect unobstructed to grater shell component 16.

Figure 4A:
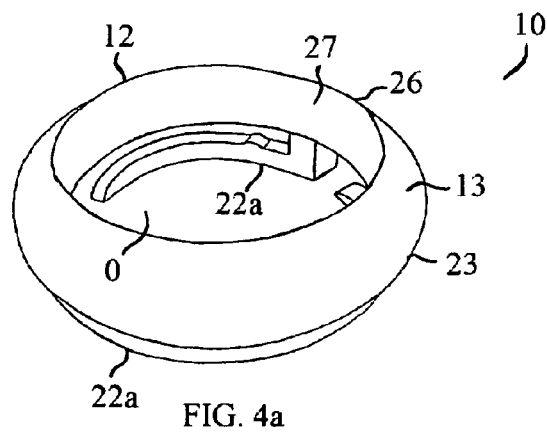
FIG. 4a, FIG. 4b, and FIG. 4c are a perspective view of the top end of three embodiments of the tapered adapter of the present application.
Figure 4B:
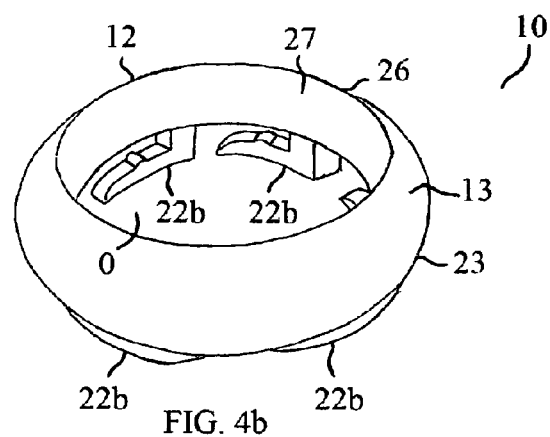
Figure 4C:
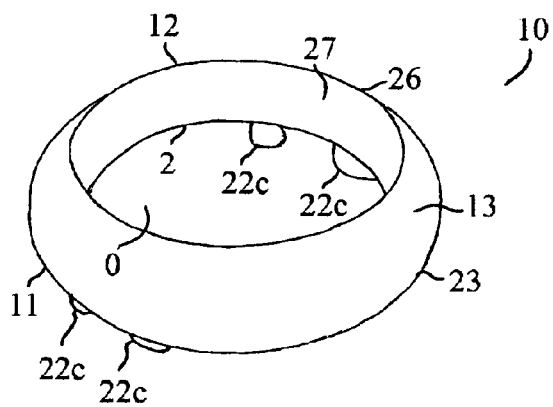

FIG. 4 is a perspective top view of an embodiment of tapered adapter 10 of the present application. The embodiment in FIG. 4 shows top end 12 having top apex 26 comprised of a smooth, blunted, rounded annular surface to facilitate unimpeded withdrawal of adapter 10 from in combination with grater shell 16 from the surgical site. Also shown in FIG. 4 is inner wall (inner portion) 27, and open portion 0 (which is the open space in the center ring of the adapter and in the center of rotation where the reamer handle passes through the adapter to connect to underlying grater shell). The embodiment in FIG. 4 shows inner wall 27 traversing longitudinally within adapter 10 between top apex 26 and an innermost circumference apex 2 (shown in FIG. 4c) of bottom end 11, along a planar path that is approximately parallel with rotational axis 21. In some embodiments, inner wall 27 may traverse between top apex 26, and bottom innermost circumference apex 2 along an arcuate path. The path along which inner wall 27 traverses is not critical so long as it allows for structural integrity of the locking mechanism and the adapter itself, it does not adversely affect the ability to withdraw adapter 10 from the surgical site unobtrusively, does not interfere with the interconnection between adapter 10 and shell component 16 when the reaming tool is in use, does not encroach upon the space needed for the distal end 15 of reamer handle 14 to connect to the shell component 16, and does not interfere with the connection of the distal end 15 of reamer handle 14 with backside 17 of shell component 16. The exceptions where the inner wall 27 must parallel the taper of the outer portion 13 of the adapter, and the bottom inner portion apex 2 of the adapter must be flush with the inner diameter of backside 17 of the grater shell would be in embodiments of an adapter that is non-removable; such as a permanently attached adapter, or a permanent portion of a grater shell where cleaning out debris within the shell would otherwise be obstructed).

The preferred embodiment in FIG. 4a has interlocking mechanism 22a protruding from bottom end 11. Referring again to FIG. 1a, interlocking mechanism 22a is comprised of one pair of curved locking bars 22a, with each curved locking bar 22a located along and following the curvature of bottom end 11, not extending into open portion 0 past plane of bottom inner portion apex 2, and not extending out further than the inner diameter of the backside 17 of grater shell. There is space for parallel portion of each curved locking bar 22a to glide easily but snugly beneath cross bar 19 on each side by a reverse twisting motion until stopped by the vertical portion of the curved locking bars 22a and by the associated locking bumps that is part of curved locking bars 22a.

The preferred embodiment in FIG. 4b has interlocking mechanism 22b protruding from bottom end 11. Referring again to FIG. 1b, interlocking mechanism 22b is comprised of two pairs of curved locking bars 22b, with each curved locking bar 22b located along and following the curvature of bottom end 11, not extending into open portion 0 past plane of bottom inner portion apex 2, and not extending out further than the inner diameter of the backside 17 of grater shell. There is space for parallel portion of each curved locking bar 22b to glide easily but snugly beneath cross bars 19 and on each side of each cross bar 19 by a reverse twisting motion until stopped by the vertical portion of the curved locking bars 22b and by the associated locking bumps that is part of curved locking bars 22b.

The embodiment in FIG. 4c has interlocking mechanism 22c protruding from bottom end 11. Referring again to FIG. 1, interlocking mechanism 22c is comprised of two pairs of leaver or clip arms, with each pair located along bottom end 11 approximately 180° from the other pair. Each locking arm 22c while located at various points along and following the curvature of bottom end 11, does not extend into open portion 0 past plane of bottom inner portion apex 2, but do lever or clip beneath the inner diameter of the backside 17 of grater shell 16 and/or around or beneath cross bar 19 of grater shell 16 depending on the style of grater shell 16. In some embodiments, interlocking mechanism 22c may be comprised of any number of snap clips in any position or configuration (not shown). In some embodiments, interlocking mechanism is comprised of one pair of snap clips and one pair of leaver arms, or any number, position, configuration, or combination of each (not shown). Each pair of leaver arms and/or snap clips is positioned and configured to firmly interlock with cross bar/s 19 and/or backside 17, to secure adapter 10 to shell component 16. In some embodiments, interlocking mechanisms 22 may comprise a rim lip (not shown), in lieu of or in addition to snap clips and/or leaver arms, that traverses the inner diameter of bottom end 11 and has contours that firmly interlock with backside 17 of shell component 16 and also may act as a buttress against the inner diameter of backside 17 as well against diagonal or lateral and rotational forces that may be exerted on adapter 10 and interlocking mechanisms 22 during the reaming procedure, introduction, or withdrawal if the shell component 16.

The use of rotational curved arm bars, snap clips, leaver arms, rim lip, rotational threads or other kind of interlocking mechanism 22, may be utilized alone or in combination with one or more other kind of interlocking mechanisms 22 in any number, position, or configuration. Such utilization is not critical so long as the interlocking mechanism(s) 22 keeps adapter 10 firmly interconnected with shell component 16 when the reaming tool is in use, does not encroach on the space needed for the distal end 15 reamer handle 14 to attach to the shell component 16, does not interfere with a smooth flush transition from shell component 16 to adapter 10, and does not interfere with the connection of the distal end 15 of reamer handle 14 with backside 17 of shell component 16.

Figure 5:
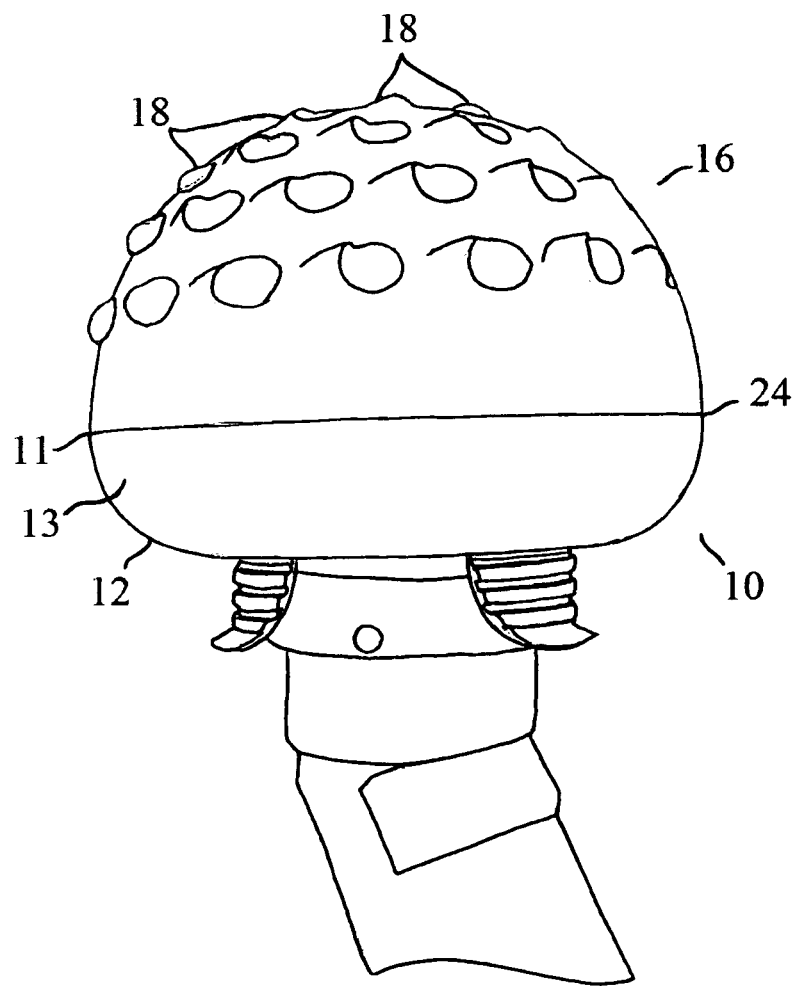
FIG. 5 is a fragmentary side view of an embodiment of the adapter of the present application attached to the grater shell component. The grater shell component is attached to a curved reamer handle.

FIG. 5 shows a fragmentary side view of an embodiment of the adapter of the present application, attached to an acetabular grater shell component 16. Adapter 10 is oriented with bottom end 11 proximal to, and flush with, backside 17 of shell component 16. Bottom end 11 has area of greater circumference and apex 23 traversing theoretical equator 24 of shell component 16. Top end 12 is distal to backside 17 and is not in contact with any portion of the distal end 15 of the reamer handle 14 or any part of the assembled reamer handle. In some embodiments the adapter may be connected to the assembled reamer handle FIG. 8. Top end 12 is the leading end of adapter 10 when the reamer is withdrawn from the surgical site following its use. Of note the bottom end 11 outer diameter 23 should always be flush with the outer diameter of the backside 17 of each individual shell component 16 to prevent any unintended snagging or damage to soft tissues by either the backside 17 on introducing the reamer into the surgical incision or of the bottom end 11 on withdrawal which would defeat the purpose of the present application.

Figure 6:
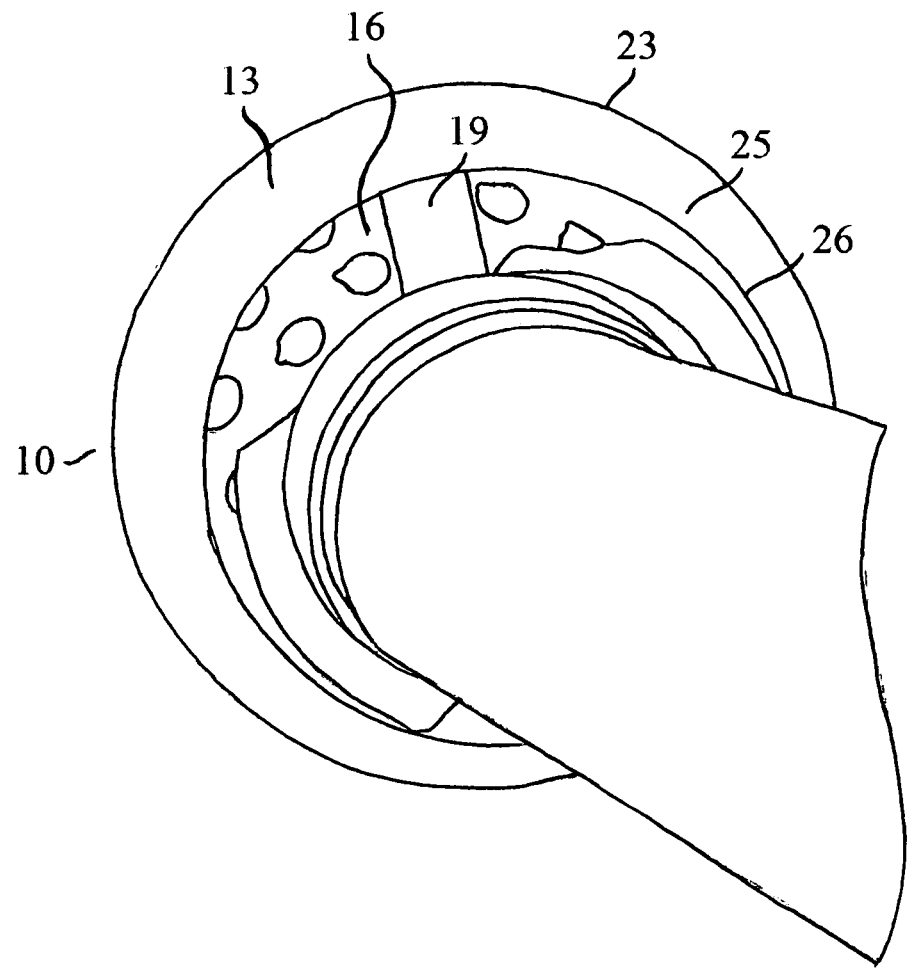
FIG. 6 is a perspective fragmentary view of the top end of an embodiment of the adapter of the present application, with the adapter attached to the grater shell component. The grater shell component is attached to a reamer handle.

FIG. 6 is a perspective fragmentary view of the top end of an embodiment of the adapter of the present application, with adapter 10 attached to the shell component 16 of an assembled acetabular reamer. With adapter 10 attached, the gradual divergence of the smooth, peripheral surface 13 of adapter 10 from area of lesser outer circumference 25 to area of greater outer circumference and apex 23, along with the rounded, blunted surface of apex 26 and the smooth flush transition from adapter 10 to shell component 16, facilitates unimpeded withdrawal of the reaming tool from the patient's body while avoiding the lodging of adapter 10 or underside 17 of shell component 16 against soft tissue.

Figure 7A:
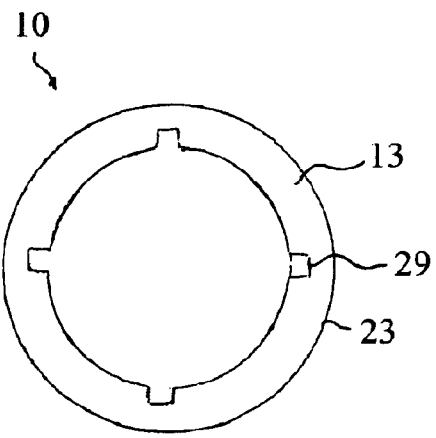
FIG. 7a, FIG. 7b, FIG. 7c, FIG. 7d, and FIG. 7e shows a face on view and side view of three embodiments of the adapter of the present application. Also shown is a face on and side view of an additional locking ring alone and attached to a standard acetabular grater that would receive an embodiment of the adapter of the present application.
Figure 7B:
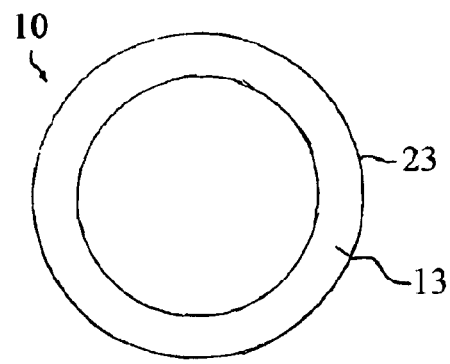
Figure 7C:
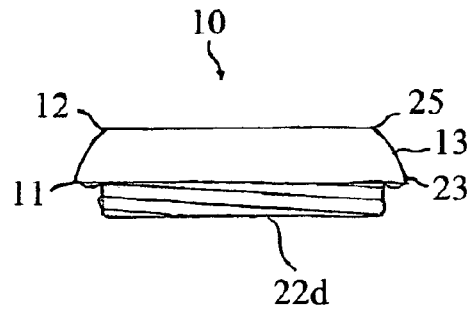
Figure 7D:
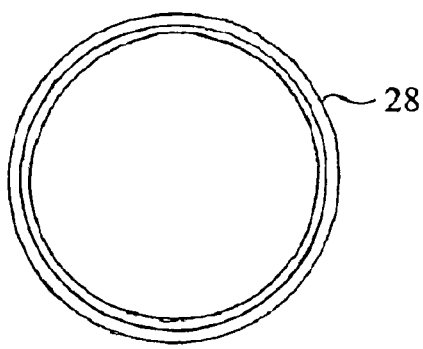
Figure 7E:
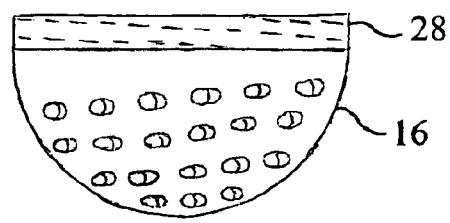

FIG. 7a, FIG. 7b, FIG. 7c, FIG. 7d, and FIG. 7e shows a face on view and side view of three embodiments of the adapter of the present application. Also shown is a face on and side view of an additional locking ring alone and attached to a standard acetabular grater that would receive an embodiment of the adapter of the present application. FIG. 7a is an example of embodiment of adapter 10 with notches/slots 29 traversing through inner wall 27 and top portion 12 at various points through top apex 26 and partly into upper outer portion 25 of outer portion 13 that would be utilized to receive a tool that would be used to attach and removed adapter 10 from backside 17 of grater shell component 16. The notches or slots shown can traverse inner wall 27 of adapter 10 from bottom inner apex 2 to top apex 26 or at any point of inner wall 27 extending to either bottom apex 2 or top apex 26 or to neither. FIG. 7b simply shows a face on view of the preferred embodiment of the adapter of the present application. FIG. 7c is an embodiment where adapter 10 has a reverse male threaded interlocking mechanism 22d. This threaded locking portion 22d is received by a female threaded ring 28 (likely metal alloy) of FIG. 7d that is added and permanently affixed to backside 17 of grater shell 16 in FIG. 7e. A face on and side view of this added ring 28 is shown in FIGS. 7d and 7e.

FIG. 8a, and FIG. 8b shows another embodiment the adapter of the present application. More specifically FIG. 8a is essentially the same drawing shown in FIG. 2 but having added an embodiment of adapter 10 that is taller and more elongated and is attached to a reamer handle 14 instead of being attached to the backside 17 of grater shell 16 cross bar/s 19. An additional locking washer 30 can be slipped over reamer handle 14 to keep adapter 10 from sliding up the reamer handle shaft away from the backside 17 of grater shell 16 during the reaming procedure. FIG. 8b shows a face on view of locking washer 30.

It is to be understood that the embodiments herein are not limited in application to the details of construction and arrangement of the components set forth in the description and illustrated in the drawings. Rather, the description and the drawings provide examples of the embodiments envisioned, but the present device is not limited to any particular embodiment or to a preferred embodiment disclosed and/or identified in the specification. The drawing figures are for illustrative purposes only, and merely provide practical examples of the application disclosed herein. Therefore, the drawing figures should not be viewed as restricting the scope of the present application to that which the drawings depict.

The present application is further capable of other embodiments and of being practiced and carried out in various ways, including various combinations and sub-combinations of the features described above but that may not have been explicitly disclosed in specific combinations and sub-combinations. Accordingly, those skilled in the art will appreciate that the conception upon which the embodiments are based may be readily utilized as a basis for the design of other structures, methods, and systems. In addition, it is understood that the phraseology and terminology employed herein are for the purpose of description and should not be regarded as limiting the present application.

What is claimed is:

1. A tapered collar adapter device that is separate from and attaches to a surgical acetabular reamer/grater for use in cooperation with said reamer/grater during a total hip joint replacement procedure comprising:
  a top portion, a bottom portion, an outer portion, an inner portion, an open portion, and an interlocking portion, wherein;
    said top portion is opposite said bottom portion, is furthest away from an attachment point or points of said adapter to an attachment point or points (peripherally) of the backside of said reamer when said adapter is attached to said reamer, is the trailing portion during insertion of said reamer, and is the leading portion during extraction of said reamer;
    said bottom portion is opposite said top portion, is in contact with or in close proximity to the backside of said reamer when attached to said reamer, is traversing the perimeter of the backside of said reamer, and is giving rise to said interlocking portion;
    said outer portion is opposite said inner portion, is opposite said open portion, and is traversing the span from said top portion to said bottom portion;

said inner portion is opposite said outer portion, is surrounding said open portion, is traversing the span from said top portion to said bottom portion;

said open portion is central to a rotation of axis, is central to and over the opening in the backside of said reamer when attached to said reamer, and is surrounded by said inner portion while allowing sufficient space for an attachment point or points of a reamer handle chuck to attach unimpeded to an attachment point or points (centrally) of the backside of said reamer;

said interlocking portion is opposite from said top portion, is arising from said bottom portion, is in intimate contact with the backside and or a cross member or members on the backside of said reamer when attached to said reamer;

at least one of said portions comprises one or more sections;

at least one of said sections further comprises one or more regions, wherein;

at least one or more of said regions comprises a smooth arcuate (curved), or ogive, or slanted, or beveling, or sloping angling taper.

2. The adapter of claim 1, wherein;
said outer portion comprises one or more regions;
at least one of said regions being an arcuate (curved), or ogive, or slanted, or beveling, or sloping angle that tapers towards the central axis of rotation extending a distance away from said bottom portion to said top portion ending at a top apex where said inner portion and said outer portion meet at said top portion.

3. The adapter of claim 1, wherein;
said outer portion of said adapter with said taper (when attached to the backside of a reamer), decreases the resistance caused by said reamer primarily during extraction, but also throughout the surgical reaming procedure including insertion, by cooperating with said reamer, and acting as an intercessory support between any soft tissue and said reamer, thus holding the soft tissues away from the backside of said reamer, thereby decreasing the angle and catch of the backside of said reamer against the soft tissues, for the purposes of decreasing a force and effort needed to extract said reamer, and for moderating injury and tissue damage that is caused by said reamer throughout said reaming procedure.

4. The adapter of claim 1, wherein;
the taper of said adapter is curved, or any shape, or angle in any combination thereof to any degree.

5. The adapter of claim 1, wherein;
the adapter generally has a symmetrical body with a smooth, or grooved, or notched said outer portion where there is an area of greater circumference at the bottom outer diameter to an area of lesser circumference at the top outer diameter, and the bottom outer diameter of said outer portion is generally flush and equal in diameter to the outer diameter of the back side of said reamers.

6. The adapter of claim 1, wherein;
the adapter generally has a symmetrical body with a smooth, or grooved, or notched said inner portion where there is an area of equal circumference at the bottom inner diameter and the top inner diameter.

7. The adapter of claim 1, wherein;
the adapter generally has a symmetrical body with a smooth, or grooved, or notched said inner portion where there is an area of greater circumference at the bottom inner diameter to an area of lesser circumference at the top inner diameter.

8. The adapter of claim 1, wherein;
the adapter is fabricated or manufactured in various incremental sizes, shapes, and interlocking portions to accommodate and match all respective sizes, shapes, types, and styles of a reamer.

9. The adapter of claim 1, wherein;
the adapter is attachable and removable from the backside of a reamer by various interlocking portions/interlocking mechanisms.

10. The adapter of claim 1, wherein;
the adapter is permanently attachable to the backside of a reamer by various welding techniques or adhesives.

11. The adapter of claim 1, wherein;
the adapter is comprised of any durable, lightweight, corrosion-resistant, surgical grade, radiolucent material, of any consistency, density, texture, rigidity, flexibility, or dimension, or combination thereof.

12. The adapter of claim 1, wherein;
the adapter is comprised of any durable, lightweight, corrosion-resistant, surgical grade, radiopaque material, of any consistency, density, texture, rigidity, flexibility, or dimension, or combination thereof.

13. The adapter of claim 1, wherein;
the adapter is of any degree of visual clarity from opaque to transparent, and of any tint, color, or combination thereof.

14. The adapter of claim 1, wherein;
the adapter is a one piece continuous tapered hemispherical ring shape, or any other shape compatible to attach to the backside shape of any reamer.

15. The adapter of claim 1, wherein;
the adapter is a modular multi-piece continuous tapered hemispherical ring shape, or any other shape compatible to the backside shape of any reamer.

16. The adapter of claim 1, wherein;
the bottom outer portion of the adapter is gapped, or marked in any way to allow for location of the transition zone between said bottom outer portion and the backside of a reamer by direct visualization or by X-ray flouro.

17. The adapter of claim 1, wherein;
the adapter incorporates notches, bumps, or slots on said inner and/or outer portions to allow the adapter to receive a tool to attach and remove said adapter from the backside of a reamer.

18. The adapter of claim 1, wherein;
the interlocking portion comprises any material, variation, position, angulation, number, shape, or combination thereof compatible with the backside shape or configuration of any reamer.

19. The adapter of claim 1, wherein;
the interlocking portion comprises a curved cam locking bar or bars, that allow the adapter to attach to, or be removed from the backside of a reamer by a clockwise or counter clockwise rotational twisting maneuver by a hand, or a tool.

20. The adapter of claim 1, wherein;
the interlocking portion comprises a clip or clips, that allow the adapter to attach to, or be removed from the backside of a reamer by a downward pushing or upward pulling maneuver by a hand, or a tool.

21. The adapter of claim 1, wherein;
the interlocking portion utilizes a screw or screws, or adhesives to attach said adapter to the backside of a reamer.

22. The adapter of claim 1, wherein;
the bottom portion of said adapter incorporates tabs or phalanges with holes to receive a screw or screws, or adhesives to attach said adapter to the backside of a reamer.

23. The adapter of claim 1, wherein;
the interlocking portion incorporates male or female threads, that allow said adapter to attach to, or be removed from the backside of a reamer by a clockwise or counter clockwise rotational twisting maneuver by a hand, or a tool.

24. The adapter of claim 1, wherein;
the interlocking portion utilizes a compression press-fit, a cold weld, or magnetics to attach said adapter to the backside of a reamer.

25. The adapter of claim 1, wherein;
the open portion of the adapter describes an axial through bore wherein;
    said open portion is configured to allow unimpeded through passage of a shaft and a chuck of a reamer handle, thereby allowing free 360 degree rotation of said adapter along an axis around said reamer handle with ample circumferential clearance of the reamer handle and the chuck.

26. A method for use of the adapter of claim 1 comprising:
1. attach said adapter to the backside of a reamer by a hand or by a tool (making sure that with each reamer size that is used that the accompanying adapter is of a matching incremental size to each reamer respectively),
2. with said adapter pre-attached to said reamer, attach the reamer to the distal end of a reamer handle, wherein the proximal end of the reamer handle will be attached to a surgical drill,
3. while holding the reamer handle, insert the reamer with the adapter together into a patient's surgical site,
4. while holding the surgical drill and the reamer handle, ream a bone with the reamer while the adapter remains attached to the reamer until desired reaming is achieved,
5. extract the reamer while the adapter remains attached to the reamer,
6. remove the reamer from the reamer handle while the adapter remains attached to the reamer,
7. remove the adapter from the reamer by a hand or by a tool to allow for the reamer to be cleaned of any debris,
   a. reattach the adapter to the backside of the reamer to ream again if desired,
8. remove the reamer from the reamer handle and choose the next desired incremental size of a reamer,
   a. then repeat steps 1-8 as necessary.

\* \* \* \* \*